US010806701B2

(12) United States Patent
Bonelli et al.

(10) Patent No.: US 10,806,701 B2
(45) Date of Patent: *Oct. 20, 2020

(54) AEROSOL FORMULATION FOR COPD

(71) Applicant: CHIESI FARMACEUTICI S.p.A., Parma (IT)

(72) Inventors: Sauro Bonelli, Parma (IT); Francesca Usberti, Parma (IT); Enrico Zambelli, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 365 days.

This patent is subject to a terminal disclaimer.

(21) Appl. No.: 14/791,553

(22) Filed: Jul. 6, 2015

(65) Prior Publication Data

US 2015/0306026 A1 Oct. 29, 2015

Related U.S. Application Data

(63) Continuation of application No. 12/977,181, filed on Dec. 23, 2010, now abandoned.

(30) Foreign Application Priority Data

Dec. 23, 2009 (EP) ..................................... 09015980

(51) Int. Cl.
| | |
|---|---|
| *A61K 9/00* | (2006.01) |
| *A61K 31/167* | (2006.01) |
| *A61K 31/40* | (2006.01) |
| *A61K 45/06* | (2006.01) |
| *A61K 47/06* | (2006.01) |
| *A61K 31/573* | (2006.01) |
| *A61K 47/10* | (2017.01) |
| *B65B 31/06* | (2006.01) |
| *B65B 31/10* | (2006.01) |

(52) U.S. Cl.
CPC ............ *A61K 9/008* (2013.01); *A61K 31/167* (2013.01); *A61K 31/40* (2013.01); *A61K 31/573* (2013.01); *A61K 45/06* (2013.01); *A61K 47/06* (2013.01); *A61K 47/10* (2013.01); *B65B 31/06* (2013.01); *B65B 31/10* (2013.01)

(58) Field of Classification Search
CPC ...... A61K 45/06; A61K 31/167; A61K 9/008; A61K 31/573; A61K 31/10; A61K 11/00; A61K 47/10
See application file for complete search history.

(56) References Cited

U.S. PATENT DOCUMENTS

| | | | |
|---|---|---|---|
| 6,475,467 | B1 | 11/2002 | Keller et al. |
| 6,716,414 | B2 | 4/2004 | Lewis et al. |
| 8,313,732 | B2 | 11/2012 | Davies et al. |
| 2004/0101483 | A1 | 5/2004 | Muller-Walz et al. |
| 2006/0257324 | A1 | 11/2006 | Lewis et al. |
| 2009/0209502 | A1 | 8/2009 | Haeberlin et al. |
| 2011/0132355 | A1 | 6/2011 | Gerhart et al. |
| 2011/0146677 | A1 | 6/2011 | Bonelli et al. |
| 2011/0150782 | A1 | 6/2011 | Bonelli et al. |
| 2011/0150784 | A1 | 6/2011 | Bonelli et al. |
| 2014/0363383 | A1 | 12/2014 | Bonelli et al. |
| 2014/0363384 | A1 | 12/2014 | Bonelli et al. |
| 2015/0182450 | A1 | 7/2015 | Bonelli et al. |
| 2015/0182459 | A1 | 7/2015 | Bonelli et al. |
| 2015/0306026 | A1* | 10/2015 | Bonelli .................. A61K 9/008 424/45 |
| 2015/0328144 | A1* | 11/2015 | Bonelli .................. A61K 9/008 424/45 |

FOREIGN PATENT DOCUMENTS

| | | |
|---|---|---|
| CA | 2 338 680 A1 | 2/2000 |
| EP | 1157689 | 11/2001 |
| EP | 1 894 568 | 3/2008 |
| WO | WO 94/13262 | 6/1994 |
| WO | WO 00/07567 A1 | 2/2000 |
| WO | 02/083079 | 10/2002 |
| WO | 2005/074900 | 8/2005 |
| WO | WO 2009/051818 | 4/2009 |

OTHER PUBLICATIONS

European Search Report in Application No. 09015980.7, dated May 12, 2010.
"Glycopyrronium Bromide" Martindale $29^{th}$ Edtion p. 532-533 (1989).
Dec. 19, 2014 Notice of Opposition in EP 2 515 854 (EP counterpart to U.S. Appl. No. 14/791,553).
Jul. 31, 2015 Reply in Opposition in EP 2 515 854 (EP counterpart to U.S. Appl. No. 14/791,553).
Jan. 28, 2016 Summons to Attend Oral Proceedings and Preliminary Opinion of Opposition Division in Opposition in EP 2 515 854 (EP counterpart to U.S. Appl. No. 14/791,553).
"Glycopyrronium Bromide" in Martindale: The Complete Drug Reference, vol. 33, 2002, p. 467.
"Glycoppyrolate," O'Neil, Maryadele J. The Merck Index: An Encyclopedia of Chemicals, Drugs, and Biologicals. Whitehouse Station, N.J: Merck, 2006.
Tzou et al. (1997), Journal of Pharmaceutical Sciences 86(12):1352-1357.
Sep. 2, 2016 Submission of Opponent in EP 2 515 854 (EP counterpart to U.S. Appl. No. 14/791,553).
Bean et al., "Advances in Pharmaceutical Sciences," Academic Press, London and New York, vol. 2, 1967, pp. 38-41.
A Study to Assess the Safety, Tolerability and Efficacy of NVA237 Versus Placebo, ClinicalTrials.gov archive view of NCT01005901, Dec. 2, 2009.
Sep. 30, 2016 Submission of Patent Owner in EP 2 515 854 (EP counterpart to U.S. Appl. No. 14/791,553).

(Continued)

*Primary Examiner* — Mina Haghighatian
(74) *Attorney, Agent, or Firm* — Oblon, McClelland, Maier & Neustadt, L.L.P.

(57) ABSTRACT

Stable aerosol solution formulations comprising glycopyrronium bromide are useful for administration to patients with COPD and other respiratory conditions.

13 Claims, No Drawings

(56) References Cited

OTHER PUBLICATIONS

Physical Property Data Sheet for Zephex 134a, retrieved from http://www.mexichemfluor.com/products/medical/zephex134a/ on Sep. 23, 2016.

Kazempour, Abdol Rassoul, "The Alkaline Hydrolysis of Esters in Aqueous-Organic Solvent Mixtures" Postgraduate School of Studies in Chemistry, Oct. 1978.

Yates K, Keith et al., "Mechanisms of Ester Hydrolysis in Aqueous Sulfuric Acids" Journal of the American Chemical Society, vol. 89, No. 11, May 24, 1967.

Carey, Francis et al., "Part A: Structure and Mechanisms" Advanced Organic Chemistry, 2000, 474-75.

Hopkinson, A.C. et al., "Acid-catalysed Hydrolysis of Alkyl Benzoates" Phys. Org, 1969.

Ferreira, Eric, "Hammett Correlations and Their Applications in Elucidating Reaction Mechanism" Stoltz Group Literature Seminar, Jul. 17, 2003.

Bender, Myron, "Mechanisms of Catalysis of Nucleophilic Reactions of Carboxylic Derivatives" Department of Chemistry, Illinois Institute of Technology, Sep. 28, 1959.

Oct. 21, 2016 Grounds for Decision in Opposition in EP 2 515 854 (EP counterpart to U.S. Appl. No. 14/791,553).

Francis A. Carey etal., Advanced Organic Chemistry, Fourth Edition, Part A: Structure and Mechanisms, Chapter 8 Reactions of Carbonyl Compounds, pp. 474-479 (1937).

D. Ganderton et al., "The Formulation and Evaluation of a CFC-Free Budesonide Pressurised Metered Dose Inhaler," Respiratory Medicine, (2003), (Supplement D), pp. 54-59.

Robert O. Williams III, et al., "Moisture Uptake and Its Influence on Pressurized Metered-Dose Inhalers", *Pharmaceutical Development and Technology*, 5(2), 153-162 (2000).

Peter Sykes, "A Guidebook to Mechanism in Organic Chemistry," *Fellow of Christ's College*, Cambridge, Longman Group Ltd., pp. 238-244 (1961).

Jerry March, Advanced Organic Chemistry, Fourth Edition, Reactions, Mechanisms, and Structure, pp. 378-398 (1929).

Andrew Streitwieser, Jr., et al., Introduction to Organic Chemistry, Second Edition, Chapter 5, pp. 86-88 and Chapter 19, pp. 539-548 (1973).

G.F. Holland et al., "Labilization of Ester Bonds in Aminocyclitol Derivatives. I. Derivatives of myo- and scyllo-Inositols and of Streptamine," Myo- and Scyllo-Inositol Derivatives, Contribution from the National Institute of Arthritis and Metabolic Diseases, National Institutes of Health, and the Naval Medical Research Institute, vol. 80 Nov. 20, 1958, pp. 6031-6035.

Thomas S. Ingallinera, et al., "Compatibility of Glycopyrrolate Injection with Commonly Used Infusion Solutions and Additives" Am. J. Hosp. Pharm. 36:508-510 Apr. 1979, with appended correction, Am. J. Hosp. Pharm. 36:745 Jun. 1979.

Acetylcholine Chloride, http://www.sigmaaldrich.com/catalog/product/sigma/a6625?lang=en&region=GB (retrieved Feb. 23, 2017).

Ranga Narayanan, "Interfacial Processes and Molecular Aggregation of Surfactants", Advances in Polymer Science, ISSN 0065-3195, p. 60 and 68-70 (2008).

Oct. 21, 2016 Decision of Opposition Division (with attached Annex) in Opposition in EP 2 515 854 (EP counterpart to U.S. Appl. No. 14/791,553).

Feb. 28, 2017 Opponent's Statement of Grounds of Appeal (with attached Annex) in Opposition in EP 2 515 854 (EP counterpart to U.S. Appl. No. 14/791,553).

Jul. 2017, Submission in Opposition Procedings in EP 2 515 855 (EP counterpart to U.S. Appl. No. 14/812,190).

Jul. 2017, Observations of the Proprietor/Respondent in Response to the Opponent's Appeal, in Opposition in EP 2 515 855 (EP counterpart to U.S. Appl. No. 14/812,190).

Christian Reichardt, "Solvents and Solvent Effects in Organic Chemistry," Third, Updated and Enlarged Edition, Wiley-VCH, pp. 93-145, 147-154, 218-237, 273-292, and 526-555 (2003).

V. Rangaiah, et al., "Effect of Polarity of the Solvent on the Acid Hydrolysis of Nitrophenyl Esters," *Indian J. Chem.*, vol. 5, pp. 483-485 (Oct. 1967).

B. Capon, et al., "A Comparison of Neighbouring Group Participation by Phenolic and Alcoholic Hydroxy-Groups in Ester Hydrolysis," *Chemical Communications*, pp. 389-390 (1971).

Enrico Emer, et al., "Direct Nucleophilic SN1-Type Reactions of Alcohol," *Microreview*, DOI 10.1002/ejoc.201001474 (2010).

K. Peter C. Vollhardt, et al., *Organic Chemistry Structure and Function*, Fifth Edition, W. H. Freeman and Company, pp. 334-337 (2007).

Huaping Mo, et al., "Closed-Shell Ion Paris: Cation and Aggregate Dynamics of Tetraalkylammonium Salts in an Ion-Pairing Solvent," *J. Am. Chem. Soc.*, vol. 119, pp. 11666-11673 (1997).

Alex Avdeef, "pH-Metric log P. Part 1. Difference Plots for Determining Ion-Pair Ocanol-Water Partition Coefficients of Multiprotic Substances," *Quant. Struct. Act. Relat.*, vol. 11, pp. 510-517 (1992).

\* cited by examiner

AEROSOL FORMULATION FOR COPD

CROSS REFERENCES TO RELATED APPLICATIONS

This application claims priority to European Patent Application No. 09015980.7 filed on Dec. 23, 2009, which is incorporated herein by reference in its entirety.

BACKGROUND OF THE INVENTION

Field of the Invention

The present invention relates to pharmaceutical aerosol solution formulations comprising glycopyrronium bromide, intended for use in pressurized metered dose inhalers. The present invention further relates to use of such formulations in the prevention and therapy of respiratory disorders, including chronic obstructive pulmonary disease (COPD).

Discussion of the Background

Glycopyrronium bromide (also known as glycopyrrolate) is a muscarinic M3 anticholinergic agent used to reduce salivation associated with administration of certain anaesthetics, and as adjunctive therapy for peptic ulcers. It has also been reported to be effective in the treatment of asthmatic symptoms (Hansel et al., *Chest*, 2005; 128:1974-1979).

WO 2005/107873 disclose the use of glycopyrrolate for the treatment of childhood asthma.

WO 01/76575 discloses a controlled release formulation for pulmonary delivery of glycopyrrolate. The formulation is intended for use in treatment of respiratory disease, in particular chronic obstructive pulmonary disease (COPD). The application focuses on dry powder formulations suitable for delivery by means of a dry powder inhaler (DPI).

One of the drawbacks of DPIs is that insufficient patient inhalation flow rates may lead to reduced dose delivery and incomplete deaggregation of the powder, leading to unsatisfactory device performance. For this reason DPIs are normally used only in older children and adults. Younger children and other people with inhalation difficulties can benefit from use of propellant-based aerosol formulations, administered by pressurized metered dose inhalers (pMDIs). pMDIs use propellant to expel droplets containing the pharmaceutical product to the respiratory tract in an aerosol.

It would be desirable to provide a clinically useful aerosol product in the form of a solution that delivers the therapeutic benefits of glycopyrronium bromide in effective and consistent doses over an extended product lifetime, and ideally without the need for storage under special conditions of temperature or humidity.

SUMMARY OF THE INVENTION

Accordingly, it is one object of the present invention to provide novel pharmaceutical aerosol solution formulations comprising glycopyrronium bromide, intended for use in pressurized metered dose inhalers.

It is another object of the present invention to provide novel methods for the prevention and therapy of respiratory disorders, including COPD.

These and other objects, which will become apparent during the following detailed description, have been achieved by the inventors' discovery that pharmaceutical compositions comprising glycopyrronium bromide dissolved in an HFA propellant, an optional co-solvent, and an amount of acid sufficient to stabilize the glycopyrronium bromide are useful for the prevention and therapy of respiratory disorders, including COPD.

Additional pharmaceutically active ingredients may also be included.

In a further aspect, the present invention provides a pressurized metered dose inhaler or other container suitable for aerosol delivery, comprising the pharmaceutical composition of the invention.

In another aspect, the present invention provides the use of pharmaceutical compositions as described herein for the therapeutic or palliative treatment or prevention of respiratory disease conditions, such as COPD.

In another aspect, the present invention provides methods for the therapeutic or palliative treatment or prevention of respiratory disease conditions, such as COPD.

DETAILED DESCRIPTION OF THE PREFERRED EMBODIMENTS

A solution formulation of glycopyrronium bromide in HFA propellant with ethanol as co-solvent was prepared and checked for stability after 3 months following storage under different conditions of temperature and humidity. One batch was stored under optimal conditions (refrigeration); the other batches were stored under accelerated degradation conditions of high temperature and humidity. Although the refrigerated batch remained stable over the 3 month period, the other batches degraded significantly over that time-span. This is the first time that glycopyrronium bromide has been observed to exhibit poor stability in any type of formulation.

Thus, a simple aerosol solution formulation of glycopyrronium bromide dissolved in propellant and co-solvent fails to meet the requirements for practical use, namely that it should be capable of being carried on the person without refrigeration and yet deliver consistent dosages of active ingredient.

The present inventors were able to overcome these stability issues by inclusion of a specific amount of inorganic acid in the formulation. In particular, they found that inclusion of an amount of 1M hydrochloric acid (HCl) in the range of 0.005 to 1.0 µg/µl, preferably 0.099-0.74 µg/µl, and more preferably 0.18-0.32 µg/µl, to the solution is sufficient to eliminate degradation of glycopyrronium bromide over an extended period of non-optimal storage, thereby ensuring a consistent dose of glycopyrronium bromide per actuation of the pMDI containing the solution formulation.

Glycopyrronium bromide, chemically defined as 3-[(cyclopentylhydroxy-phenylacetyl)oxy]-1,1-dimethylpyrrolidinium bromide, has two chiral centers corresponding to four potential different stereoisomers with configurations (3R,2'R), (3S,2'R), (3R,2'S), and (3S,2'S). Glycopyrronium bromide in the form of any of these pure enantiomers or diastereomers or any combination thereof may be used in practising the present invention. In one embodiment of the present invention, the (3S,2'R),(3R,2'S)-3-[(cyclopentylhydroxyphenylacetyl)oxy]-1,1-dimethylpyrrolidinium bromide racemic mixture, also known as glycopyrrolate is preferred. Glycopyrronium bromide is present in the formulation in an amount in the range from 0.005 to 0.14% (w/w), preferably from 0.010 to 0.13% (w/w), more preferably from 0.015 to 0.04% (w/w), wherein % (w/w) means the amount by weight of the component, expressed as percent with respect to the total weight of the composition.

Glycopyrrolate is commercially available, and can be synthesized according to the process described in U.S. Pat. No. 2,956,062 or in Franko B V and Lunsford C D, *J. Med. Pharm. Chem.*, 2(5), 523-540, 1960.

The propellant component of the composition may be any pressure-liquefied propellant and is preferably a hydrofluoroalkane (HFA) or a mixture of different HFAs, more preferably selected from the group consisting of HFA134a (1,1,1,2-tetrafluoroethane), HFA 227 (1,1,1,2,3,3,3-heptafluoropropane, and mixtures thereof. The preferred HFA is HFA134a. HFAs may be present in the formulation in an amount in the range from 75 to 95% (w/w), preferably from 85 to 90% (w/w), wherein % (w/w) means the amount by weight of the component, expressed as percent with respect to the total weight of the composition.

The co-solvent incorporated into formulation of the present invention has a higher polarity than that of the propellant and may include one or more substances such as a pharmaceutically acceptable alcohol, in particular ethanol, or a polyol such as propylene glycol or polyethylene glycol.

Advantageously the co-solvent is selected from the group of lower branched or linear alkyl ($C_1$-$C_4$) alcohols such as ethanol and isopropyl alcohol. Preferably the co-solvent is ethanol.

The concentration of the co-solvent will vary depending on the final concentration of the active ingredient in the formulation and on the type of propellant. For example ethanol may be used in a concentration comprised in the range from 5 to 25% (w/w), preferably from 8 to 20% (w/w), more preferably from 10 to 15% (w/w), wherein % (w/w) means the amount by weight of the component, expressed as percent with respect to the total weight of the composition. In one of the preferred embodiments, the concentration of ethanol is 12% (w/w).

The ratio of propellant to co-solvent in the formulation is preferably in the range 50:50 to 95:5 (w/w).

It is envisaged that HCl of a different molarity or alternative inorganic acids (mineral acids) could substitute for 1M HCl in the formulations of the invention. For instance, alternative acids could be any pharmaceutically acceptable monoprotic or polyprotic acid, such as (but not limited to): hydrogen halides (hydrochloric acid hydrobromic acid, hydroiodic acid etc.) phosphoric acid, nitric acid, sulphuric acid, and halogen oxoacids.

The pharmaceutically active components of the composition are preferable completely and homogeneously dissolved in the mixture of propellant and co-solvent, i.e. the composition is preferably a solution formulation.

Optionally, the solution formulation compositions may comprise other pharmaceutical excipients or additives known in the art. In particular, the compositions of the present invention may comprise one or more low volatility components. Low volatility components are useful in order to increase the mass median aerodynamic diameter (MMAD) of the aerosol particles upon actuation of the inhaler and/or to improve the solubility of the active ingredient in the propellant/co-solvent mixture.

The low volatility component, when present, has a vapor pressure at 25° C. lower than 0.1 kPa, preferably lower than 0.05 kPa. Examples of low-volatility components may be esters such as isopropyl myristate, ascorbyl myristate, tocopherol esters; glycols such as propylene glycol, polyethylene glycol, glycerol; or surface active agents such as a saturated organic carboxylic acid (i.e. lauric, myristic, stearic acid) or an unsaturated carboxylic acid (i.e. oleic or ascorbic acid).

The amount of low volatility component may vary from 0.1 to 10% w/w, preferably from 0.5 to 5% (w/w), more preferably between 1 and 2% (w/w), wherein % (w/w) means the amount by weight of the component, expressed as percent with respect to the total weight of the composition.

In one embodiment of the present invention, an amount of water comprised between 0.005 and 0.5% (w/w), wherein % (w/w) means the amount by weight of the component, expressed as percent with respect to the total weight of the composition, may optionally be added to the formulations in order to favourably affect the solubility of the active ingredient without increasing the MMAD of the aerosol droplets upon actuation.

Advantageously, the formulations of the present invention are free of excipients (such as surfactants) other than the co-solvent, the propellant, and a stabilizing amount of an acid.

The present invention also relates to a method for preparing a pharmaceutical composition, comprising adding 1M HCl to a solution of glycopyrronium bromide in HFA propellant and co-solvent, wherein the amount of 1M HCl added is in the range of 0.005 to 1.0 µg per µl of the final solution.

The pharmaceutical compositions of the present invention may further comprise other, additional pharmaceutically active agents for separate, sequential or simultaneous use. Optional additional pharmaceutically active components of the composition include any known in the art for prophylaxis or treatment of respiratory diseases and their symptoms. Examples of these active components are: beta-2-agonists such as formoterol, salbutamol, fenoterol, carmoterol (TA 2005), indacaterol, milveterol, vilanterol (GSK 642444), terbultaline, salmeterol, bitolterol, metaproterenol all in form of single stereoisomers or mixtures thereof and salts thereof; corticosteroids such as beclometasone dipropionate, fluticasone propionate, butixocort, mometasone furoate, triamcinolone acetonide, budesonide and its 22R-epimer, ciclesonide, flunisolide, loteprednol, and rofleponide; other anti-muscarinic drugs such as methscopolamine, ipratropium bromide, oxitropium bromide and tiotropium bromide; phosphodiesterase IV inhibitors such as: cilomilast, roflumilast and tetomilast. Among these additional active components formoterol fumarate is particularly preferred.

The compositions of the present invention can be inhaled from any suitable MDI device known to the skilled person. Desired doses of the individual pharmaceutically active components of the formulation are dependent on the identity of the component and the type and severity of the disease condition, but are preferably such that a therapeutic amount of the active ingredient is delivered in one or two actuations. Generally speaking, doses of active ingredient are in the range of about 0.5 µg to 1000 µg per actuation, e.g. about 1 to 100 µg/actuation, and sometimes about 5 to 50 µg/actuation. The skilled person in the field is familiar with how to determine the appropriate dosage for each individual pharmaceutically active ingredient.

With specific reference to glycopyrronium bromide, the preferred dosage is about 0.5 to 100 µg per actuation, preferably about 1 to 40 µg per actuation, more preferably about 5 to 26 µg per actuation, even more preferably 25 µg per actuation.

The pharmaceutical formulation of the present invention is filled into pMDI devices known in the art. Said devices comprise a canister fitted with a metering valve. Actuation of the metering valve allows a small portion of the spray product to be released. Part or all of the canister may be made of a metal, for example aluminium, aluminium alloy, stainless steel or anodized aluminium. Alternatively the canister may be a plastic can or a plastic-coated glass bottle.

The metal canisters may have part or all of the internal surfaces lined with an inert organic coating. Examples of preferred coatings are epoxy-phenol resins, perfluorinated polymers such as perfluoroalkoxyalkane, perfluoroalkoxyalkylene, perfluoroalkylenes such as poly-tetrafluoroethylene (Teflon), fluorinated-ethylene-propylene (FEP), polyether sulfone (PES) or fluorinated-ethylene-propylene polyether sulfone (FEP-PES) mixtures or combination thereof. Other suitable coatings could be polyamide, polyimide, polyamideimide, polyphenylene sulfide or their combinations.

In certain embodiments, canisters having the internal surface lined with FEP-PES or Teflon may preferably be used.

In other particular embodiments, canisters made of stainless steel may be used.

The container is closed with a metering valve for delivering a daily therapeutically effective dose of the active ingredient. Generally, the metering valve assembly comprises a ferrule having an aperture formed therein, a body moulding attached to the ferrule which houses the metering chamber, a stem consisting of a core and a core extension, an inner- and an outer-seal around the metering chamber, a spring around the core, and a gasket to prevent leakage of propellant through the valve.

The gasket seal and the seals around the metering valve may comprise elastomeric material such as EPDM, chlorobutyl rubber, bromobutyl rubber, butyl rubber, or neoprene. EPDM rubbers are particularly preferred. The metering chamber, core and core extension are manufactured using suitable materials such as stainless steel, polyesters (e.g. polybutyleneterephthalate (PBT)), or acetals. The spring is manufactured in stainless steel eventually including titanium. The ferrule may be made of a metal, for example aluminum, aluminum alloy, stainless steel or anodized aluminum. Suitable valves are available from manufacturers such as Valois, Bespak plc and 3M-Neotechnic Ltd.

The pMDI is actuated by a metering valve capable of delivering a volume of between 25 to 100 µl, preferably between 40 to 70 µl and optionally about 50 µl, or about 63 µl per actuation.

Each filled canister is conveniently fitted into a suitable channeling device prior to use to form a metered dose inhaler for administration of the medicament into the lungs of a patient. Suitable channeling devices comprise, for example, a valve actuator and a cylindrical or cone-like passage through which medicament may be delivered from the filled canister via the metering valve to the mouth of a patient e.g. a mouthpiece actuator.

In a typical arrangement, the valve stem is seated in a nozzle block which has an orifice leading to an expansion chamber. The expansion chamber has an exit orifice which extends into the mouthpiece. Actuator (exit) orifices having a diameter in the range 0.15 to 0.45 mm and a length from 0.30 to 1.7 mm are generally suitable. Preferably an orifice having a diameter from 0.2 to 0.44 mm is used, e.g. 0.22, 0.25, 0.30, 0.33 or 0.42 mm.

In certain embodiments of the present invention, it may be useful to utilize actuator orifices having a diameter ranging from 0.10 to 0.22 mm, in particular from 0.12 to 0.18 mm, such as those described in WO 03/053501. The use of said fine orifices may also increase the duration of the cloud generation and hence, may facilitate the coordination of the cloud generation with the slow inspiration of the patient.

In case the ingress of water into the formulation is to be avoided, it may be desired to overwrap the MDI product in a flexible package capable of resisting water ingress. It may also be desirable to incorporate a material within the packaging which is able to adsorb any propellant and co-solvent which may leak from the canister (e.g. a molecular sieve).

Optionally, the MDI device filled with the formulation of the present invention may be utilized together with suitable auxiliary devices favoring the correct use of the inhaler. Said auxiliary devices are commercially available and, depending on their shape and size, are known as "spacers", "reservoirs" or "expansion chambers". Volumatic™ is, for instance, one of the most widely known and used reservoirs, while Aerochamber™ is one of the most widely used and known spacers. A suitable expansion chamber is reported for example in WO 01/49350.

The formulation of the present invention may also be used with common pressurized breath-activated inhalers such as those known with the registered names of Easi-Breathe™ and Autohaler™.

The efficacy of an MDI device is a function of the dose deposited at the appropriate site in the lungs. Deposition is affected by the aerodynamic particle size distribution of the formulation which may be characterized in vitro through several parameters.

The aerodynamic particle size distribution of the formulation of the invention may be characterized using a Cascade Impactor according to the procedure described in the European Pharmacopoeia $6^{th}$ edition, 2009 (6.5), part 2.09.18. An Apparatus E, operating at a flow rate range of 30 litres/minute to 100 litres/minute or an Apparatus D—Andersen Cascade Impactor (ACI)-, operating at a flow rate of 28.3 l/minute, may be utilized. Deposition of the drug on each ACI plate is determined by high performance liquid chromatography (HPLC).

The following parameters of the particles emitted by a pressurized MDI may be determined:

i) mass median aerodynamic diameter (MMAD) is the diameter around which the mass aerodynamic diameters of the emitted particles are distributed equally;

ii) delivered dose is calculated from the cumulative deposition in the ACI, divided by the number of actuations per experiment;

iii) respirable dose (fine particle dose=FPD) is obtained from the deposition from Stages 3 (S3) to filter (AF) of the ACI, corresponding to particles of diameter ≤4.7 microns, divided by the number of actuations per experiment;

iv) respirable fraction (fine particle fraction=FPF) which is the percent ratio between the respirable dose and the delivered dose; and v) "superfine" dose is obtained from the deposition from Stages 6 (S6) to filter, corresponding to particles of diameter ≤1.1 microns, divided by the number of actuations per experiment.

The solutions of the present invention are capable of providing, upon actuation of the pMDI device in which they are contained, a total FPF higher than 40%, preferably higher than 50%, more preferably higher than 60%.

Moreover, the formulations of the present invention are capable of providing, on actuation, a fraction higher than or equal to 30% of emitted particles of diameter equal to or less than 1.1 microns as defined by the content stages S6-AF of an Andersen Cascade Impactor, relative to the total fine particle dose collected in the stages S3-AF of the impactor. Preferably the fraction of emitted particles of diameter equal to or less than 1.1 microns is higher than or equal to 40%, more preferably higher than 50%, even more preferably higher than 60%, most preferably higher than 70%.

According to a further aspect of the present invention there is provided a method of filling an aerosol inhaler with a composition of the present invention. Conventional bulk manufacturing methods and machinery well known to those skilled in the art of pharmaceutical aerosol manufacture may be employed for the preparation of large-scale batches for the commercial production of filled canisters.

The method comprises:
a) preparing a solution comprising glycopyrronium bromide, a co-solvent (e.g. ethanol), a mineral acid, a propellant comprising a HFA and optionally a low volatility component at a temperature from −50 to −60° C. at which the solution does not vaporize;
b) cold filling the inhaler with the prepared solution; and
c) placing the valve onto the can and crimping.

An alternative method comprises:
a) preparing a solution comprising glycopyrronium bromide, a co-solvent (e.g. ethanol), a mineral acid, and optionally a low volatility component;
b) filling the open can with the bulk solution;
c) placing the valve onto the can and (vacuum) crimping; and
d) pressure-filling the can with HFA propellant through the valve.

A further alternative method comprises:
a) preparing a solution comprising glycopyrronium bromide, a co-solvent (e.g. ethanol), a mineral acid, an optional low volatility component and HFA propellant using a pressurised vessel:
b) placing the valve onto the empty can and crimping; and
c) pressure-filling the can with the final solution formulation through the valve.

The packaged formulations of the present invention are stable for extended periods of time when stored under normal conditions of temperature and humidity. In a preferred embodiment, the packaged formulations are stable for at least 6 months at 25° C. and 60% RH, more preferably for at least 1 year, most preferably for at least 2 years. Stability is assessed by measuring content of residual active ingredient. A "stable" formulation as defined herein means one retaining at least about 85%, preferably at least about 90%, and most preferably at least about 95% of residual content of each active ingredient at a given time point, as measured by HPLC-UV VIS.

The optimized stable formulations meet the specifications required by the ICH Guideline Q1B or CPMP/QWP/122/02 Rev. 1 relevant for drug product stability testing for the purposes of drug registration.

The product of the present invention may be used for prophylactic purposes or for symptomatic relief of a wide range of respiratory disorders, such as asthma of all types and chronic obstructive pulmonary disease (COPD).

Other respiratory disorders for which use of the pharmaceutical compositions of the present invention may be beneficial are those characterized by obstruction of the peripheral airways as a result of inflammation and presence of mucus, such as chronic obstructive bronchiolitis, chronic bronchitis, emphysema, acute lung injury (ALI), cystic fibrosis, rhinitis, and adult or acute respiratory distress syndrome (ARDS).

Other features of the invention will become apparent in the course of the following descriptions of exemplary embodiments which are given for illustration of the invention and are not intended to be limiting thereof.

EXAMPLES

Example 1

Glycopyrronium Bromide Stability During Storage with or without Acid Addition

Solution formulations were prepared with the compositions shown in Table 1.

TABLE 1

Composition of the tested Gly pMDI solution formulations.

Theoretical Unit Formula (μg/actuation for a 63 μl valve)

| | Glycopyrronium bromide (GLY) | Anhydrous ethanol | 1M HCl | HFA 134a | Total |
|---|---|---|---|---|---|
| Without Acid | 25 | 8856 | — | 64919 | 73800 |
| With Acid | 25 | 8856 | 14 | 64905 | 73800 |

The samples containing acid were formulated by the addition of 1M HCl in an amount corresponding to 0.222 μg/μl of the solution. The solution was filled into canisters which were stored inverted under different conditions: 5°; 25° C./60% RH; 30° C./75% RH; 40° C./75% RH. The samples were analyzed chromatographically for glycopyrronium bromide content after 1 to 3 months of storage and after 6 months storage only for 5°; 25° C./60% RH. The results are reported in the following Table 2.

TABLE 2

GLY pMDI can content (mean % residue ± standard deviation).

| Temperature/ relative humidity | Glycopyrronium Bromide (without acid) | | | | Glycopyrronium Bromide (with acid) | | | |
|---|---|---|---|---|---|---|---|---|
| | 1M | 2M | 3M | 6M | 1M | 2M | 3M | 6M |
| 5° C. | 98.4 ± 0.9 | 99.9 ± 1.3 | 99.3 ± 2.1 | 99.6 ± 0.4 | 102.8 ± 1.1 | 101.4 ± 0.5 | 103.3 ± 0.4 | 103.5 ± 0.4 |
| 25° C./60% | 93.8 ± 1.4 | 91.3 ± 0.7 | 90.3 ± 1.1 | 84.2 ± 0.2 | 101.7 ± 0.7 | 101.9 ± 0.5 | 102.7 ± 0.0 | 102.8 ± 0.4 |
| 30° C./75% | 90.5 ± 4.2 | 87.8 ± 1.8 | 88.9 ± 2.3 | — | 101.1 ± 1.2 | 100.7 ± 0.0 | 102.3 ± 0.4 | — |
| 40° C./75% | 92.5 ± 3.1 | 88.4 ± 4.7 | 80.2 ± 1.9 | — | 100.1 ± 2.4 | 101.8 ± 0.4 | 102.0 ± 1.4 | — |

As shown in Table 2, GLY was relatively unstable when stored under suboptimal conditions. After 3 months at 40° C./75% RH, the content of GLY in the samples decreased to about 80%. However, in the presence of acid there was no significant degradation of GLY at 3 months, irrespective of the storage conditions. The obtained data at 5°; 25° C./60% RH show that in presence of acid the product can be stored both in normal and accelerated conditions, whereas without acid it is not possible to store it at 25° C./60% RH.

Example 2

Glycopyrronium Bromide Stability During Storage with Different Amount of HCl Solution formulations were prepared with a composition corresponding to that of Example 1, Table 1, added with the following different amounts of 1 M HCl.

| 1M HCl | |
|---|---|
| µg/actuation (for a 63 µl valve) | µg/µl of the formulation |
| 0.312 | 0.0050 |
| 3.13 | 0.0497 |
| 6.25 | 0.0992 |
| 11.8 | 0.187 |
| 15.6 | 0.248 |
| 20.6 | 0.327 |
| 25.0 | 0.397 |
| 28.1 | 0.446 |
| 46.8 | 0.743 |
| 65.6 | 1.041 |

The solutions were filled into conventional aluminium canisters provided with EPDM valves which were stored inverted for 1 month at 40° C./75% RH. The samples were analyzed chromatographically for glycopyrronium bromide content, and the values are the mean values from three cans.

No stability issues were found for the whole range of acid concentrations.

The residual glycopyrronium bromide content ranged from 95.9±0.5% to 101.9±2.4% with respect to the content at time 0, and the total degradation product ranged from 0.8±0.1% to 3.7±1.0% of the total composition. Moreover when the concentrations of the acid was lower than 0.187 µg/µl or higher than 0.743 µg/µl, less residual active ingredient, higher levels of degradation products, and more variability of their levels were obtained.

Therefore, stable glycopyrronium bromide HFA solution formulations may be obtained by using an amount of 1M hydrochloric acid (HCl) in the range of 0.005 to 1.0 µg/µl, preferably of 0.099 to 0.74 µg/µl, and more preferably 0.18 to 0.32 µg/µl.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A pharmaceutical composition for use with a pressurized metered dose inhaler, comprising glycopyrronium bromide dissolved in HFA-134a and ethanol, wherein:
    the composition comprises an amount of hydrochloric acid equivalent to 0.005 to 1.0 µg/µl of 1M hydrochloric acid;
    the composition comprises glycopyrronium bromide in an amount of 0.015 to 0.04% w/w of the composition;
    the composition comprises ethanol in an amount of 10 to 15% w/w of the composition; and
    the composition comprises HFA-134a in an amount of 85 to 90% w/w of the composition.

2. A composition according to claim 1, comprising an amount of hydrochloric acid equivalent to 0.18 to 0.32 µg/µl 1M hydrochloric acid.

3. A composition according to claim 1, comprising one or more pharmaceutically active ingredients selected from the group consisting of beta-2-agonists, corticosteroids, antimuscarinic agents, and phosphodiesterase (IV) inhibitors.

4. A composition according to claim 3, comprising formoterol fumarate.

5. A composition according to claim 3, comprising beclomethasone dipropionate.

6. A metered dose inhaler, comprising a pharmaceutical composition according to claim 1.

7. A kit-of-parts, comprising:
    a pharmaceutical composition according to claim 1; and
    one or more pharmaceutically active ingredients for separate, sequential, or simultaneous administration;
    wherein the one or more pharmaceutically active ingredients are selected from the group consisting of beta-2-agonists, corticosteroids, antimuscarinic agents, and phosphodiesterase (IV) inhibitors.

8. A composition according to claim 1, wherein the composition comprises an amount of hydrochloric acid equivalent to 0.099 to 0.74 µg/µl of 1M hydrochloric acid.

9. A metered dose inhaler according to claim 6, comprising a metering valve capable of delivering a volume of about 63 µl per actuation.

10. A composition according to claim 1, wherein the glycopyrronium bromide is the racemic mixture (3S,2'R), (3R,2'S)-3-[(cyclopentylhydroxyphenylacetyl)oxy]-1,1-dimethylpyrrolidinium bromide.

11. A composition according to claim 1, comprising water in an amount less than 0.5% w/w of the composition.

12. A composition according to claim 1, comprising water in an amount 0.005 to 0.5% w/w of the composition.

13. A composition according to claim 1, wherein the composition is free of excipients other than the ethanol, the HFA-134a, and the hydrochloric acid.

* * * * *

UNITED STATES PATENT AND TRADEMARK OFFICE
CERTIFICATE OF CORRECTION

PATENT NO. : 10,806,701 B2
APPLICATION NO. : 14/791553
DATED : October 20, 2020
INVENTOR(S) : Sauro Bonelli et al.

It is certified that error appears in the above-identified patent and that said Letters Patent is hereby corrected as shown below:

On the Title Page

Column 2, item (56), Other Publications, Line 3, "Edtion" should read -- Edition --, Column 2, item (56), Other Publications, Line 14, "Glycoppyrolate" should read -- Glycopyrrolate --, Page 2, Column 1, item (56), Other Publications, Line 22, "etal.," should read -- et al., --, Page 2, Column 2, item (56), Other Publications, Line 20, "Procedings" should read -- Proceedings --, Page 2, Column 2, item (56), Other Publications, Line 43, "Ocanol" should read -- Octanol --, In the Specification Column 3, Lines 5-6, "heptafluoropropane" should read -- heptafluoropropane) --, Column 5, Line 39, "70 µl" should read -- 70 μl, --, In the Claims Column 10, Line 18, Claim 2, "1M" should read -- of 1M --.

Signed and Sealed this
Seventh Day of June, 2022

Katherine Kelly Vidal
*Director of the United States Patent and Trademark Office*